(12) United States Patent
Kanakkanatt et al.

(10) Patent No.: US 9,259,974 B2
(45) Date of Patent: Feb. 16, 2016

(54) LONG-TERM INDICATOR FOR RUBBER ARTICLES

(71) Applicants: Bridgestone Corporation, Tokyo (JP); Bridgestone Research, LLC, Akron, OH (US)

(72) Inventors: Sebastian V. Kanakkanatt, Akron, OH (US); Hiroshi Mouri, Bath, OH (US); Santosh B. Kanakkanatt, Akron, OH (US)

(73) Assignees: Bridgestone Corporation, Tokyo (JP); Bridgestone Research, LLC, Akron, OH (US)

( * ) Notice: Subject to any disclaimer, the term of this patent is extended or adjusted under 35 U.S.C. 154(b) by 0 days.

(21) Appl. No.: 14/215,360

(22) Filed: Mar. 17, 2014

(65) Prior Publication Data

US 2014/0275333 A1 Sep. 18, 2014

Related U.S. Application Data

(60) Provisional application No. 61/799,413, filed on Mar. 15, 2013.

(51) Int. Cl.
*C08J 9/32* (2006.01)
*B60C 11/24* (2006.01)
*B60C 13/00* (2006.01)

(52) U.S. Cl.
CPC .............. *B60C 11/24* (2013.01); *B60C 13/00* (2013.01); *G01N 2203/06* (2013.01); *G01N 2203/0605* (2013.01)

(58) Field of Classification Search
CPC .................. B60C 11/24; G01N 2203/0605
USPC ........................................ 523/218; 252/408.1
See application file for complete search history.

(56) References Cited

U.S. PATENT DOCUMENTS

| | | | |
|---|---|---|---|
| 3,018,611 | A | 1/1962 | Biritz |
| 4,212,153 | A | 7/1980 | Kydonieus et al. |
| 4,229,813 | A | 10/1980 | Lilly et al. |
| 4,382,700 | A | 5/1983 | Youngren |
| 4,408,557 | A | 10/1983 | Bradley et al. |
| 4,629,330 | A | 12/1986 | Nichols |
| 4,643,122 | A | 2/1987 | Seybold |
| 4,903,254 | A | 2/1990 | Haas |
| 5,058,088 | A | 10/1991 | Haas et al. |
| 5,085,802 | A | 2/1992 | Jalinski |
| 5,107,470 | A | 4/1992 | Pedicano et al. |
| 5,476,792 | A | 12/1995 | Ezrielev et al. |
| 5,602,804 | A | 2/1997 | Haas |

*Primary Examiner* — Edward Cain
(74) *Attorney, Agent, or Firm* — Meredith E. Hooker; Arthur M. Reginelli

(57) ABSTRACT

A rubber article comprising: a rubber substrate; and an indicator carried by said rubber substrate, said indicator including at least one component including porous ceramic particles that are at least partially saturated with a liquid, where the particles are transparent when at least saturated with the liquid.

17 Claims, 3 Drawing Sheets

LONG-TERM INDICATOR FOR RUBBER ARTICLES

This application claims the benefit of U.S. Provisional Application Ser. No. 61/799,413, filed on Mar. 15, 2013, which is incorporated herein by reference.

FIELD OF THE INVENTION

Embodiments of the present invention are directed toward a time indicator that is useful with rubber articles such as tires and airsprings. The time indicator provides a visual indication after an extended time period, where the time period is generally indicative of the useful service life of the rubber article.

BACKGROUND OF THE INVENTION

Rubber articles, such as tires and airsprings, generally have a limited service life. This service life may be defined in terms of wear, such as in the situation of a tire where the tread wears through road contact. Service life may also be defined by fatigue stress where rubber articles that undergo repeated dynamic cycles begin to fatigue as a result of these cycles. Still further, the useful life of a rubber article may be limited by age.

While service life limited by wear and/or fatigue may be visible to the user, it may be difficult to gauge any service life limitations that relate to age. Accordingly, there is a desire for an indicator that can offer insight as to the age of a rubber article, such as a tire or airspring.

SUMMARY OF THE INVENTION

Embodiments of the present invention provide a rubber article comprising a rubber substrate and an indicator carried by said rubber substrate, said indicator including at least one component including porous ceramic particles that are at least partially saturated with a liquid, where the particles are transparent when at least saturated with the liquid.

DETAILED DESCRIPTION OF ILLUSTRATIVE EMBODIMENTS

Figure 1:
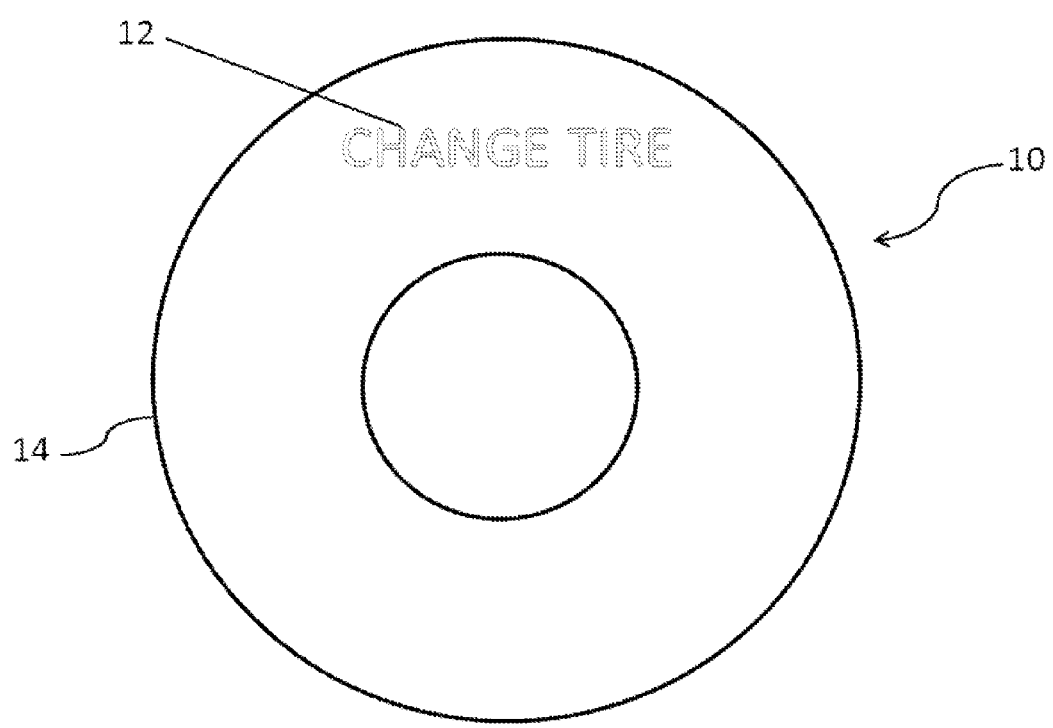
FIG. 1 is a perspective view of a tire according to one or more embodiments of the present invention.

Embodiments of the present invention are based, at least in part, on the discovery of a long-term indicator. The indicator can advantageously be used on a rubber articles, such as a tire or airspring, to provide an indication of age. In one or more embodiments, the indicator takes advantage of the phenomenon that certain porous solids can be made transparent when they absorb certain liquids, and upon depletion or loss of the liquid, such as through evaporation, the porous solids return to their generally opaque or translucent state and thereby provide a visual indication of a time lapse. Advantageously, this phenomenon works over a long time period, which time period can be commensurate with the useful life of a rubber article. Moreover, the selection of the raw materials (e.g., the porous solid and the liquid) can be used to tailor the time interval so as to make the indicator more useful with various rubber articles. Thus, while various indicator labels are known in the art, including those used in conjunction with tires, the present invention overcomes one or more problems associated with the prior art by providing an indicator that is highly visible, operates over a long time duration, and can be fabricated to have high durability.

Indicator Composition

In one or more embodiments, the indicator of the present invention includes a component including a porous solid. In one or more embodiments, the component is a layer or coating in which the porous solid is contained. The porous solid may be in the form of porous particles dispersed within a binder matrix. The combination of the porous particles and the binder, as well as any other constituents dispersed within the binder matrix, may be referred to as the indicator composition.

Porous Particles

In one or more embodiments, the porous particles include porous ceramics. As the skilled person understands, porous ceramic materials refract light at their pore boundaries, which results in the particles being opaque or at least translucent. Accordingly, the porous ceramics employed in one or more embodiments of this invention have sufficient porosity to refract sufficient light to make the porous ceramic particles readily visible and therefore useful within the indicators of the invention.

In one or more embodiments, the porous ceramic materials include silica. As is generally known, silica refers to the generally pure form of silicon dioxide. Silica can be manufactured in several forms including fused quartz, crystal, fumed silica, colloidal silica, silica gel, and aerogel. In other embodiments, the porous ceramic material is a silicate. As is generally known, silicates include a silicon-containing anion (e.g., $SiO_4^-$) balanced by various cations (e.g., $Na^+$ and $Al^{+3}$). The compositional and physical characteristics of silicates can be adjusted by using precipitation technologies. These engineered materials may generally be referred to as precipitated silicas or precipitated silicates.

In one or more embodiments, the porous ceramic material is a sodium aluminosilicate. In particular embodiments, synthetic amorphous sodium aluminosilicates are employed. In one or more embodiments, the sodium aluminosilicates may be represented by the molecular formula $AlNa_{12}SiO_5$.

In one or more embodiments, the sodium aluminosilicates have a sodium content at most 5.0 weight percent, in other embodiments at most 1.0 weight percent, and in other embodiments at most 0.6 weight percent. In these or other embodiments, the sodium aluminosilicates have a sodium content in the range from about 0.0 to about 10.0 weight percent, in other embodiments from about 4.0 to about 6.0 weight percent, and in other embodiments from about 4.8 to about 5.2 weight percent.

In one or more embodiments, the sodium aluminosilicates have an aluminum content of at most 6.5 weight percent, in other embodiments at most 1.0 weight percent, and in other embodiments at most 0.5 weight percent. In these or other embodiments, the sodium aluminosilicates have an aluminum content in the range from about 0.0 to about 10.0 weight percent, in other embodiments from about 5.5 to about 7.5 weight percent, and in other embodiments from about 6.3 to about 6.7 weight percent.

In one or more embodiments, the sodium aluminosilicates have a silica content of at least 81 weight percent, in other embodiments at least 87 weight percent, and in other embodiments at least 97 weight percent. In these or other embodiments, the sodium aluminosilicates have a silica content in the range from about 71.0 to about 91.0 weight percent, in other embodiments from about 76.0 to about 86.0 weight percent, and in other embodiments from about 80.0 to about 82.0 weight percent.

In one or more embodiments, the sodium aluminosilicate particles may be characterized by a particle size, which may be an agglomerate average particle size, in the range from about 1 to about 350 µm, in other embodiments from about 3 to about 150 µm, in other embodiments from about 6 to about 120 µm, and in other embodiments from about 1 to about 25 µm. As the skilled person appreciates, the particle size can be determined by laser diffraction as per ISO 13320-1.

In one or more embodiments, the sodium aluminosilicate may be characterized by a specific surface area in the range from about 1 to about 500 $m^2/g$, in other embodiments from about 50 to about 200 $m^2/g$, and in other embodiments from about 75 to about 100 $m^2/g$. As the skilled person appreciates, the surface area can be determined by multipoint as per ISO 9277.

In one or more embodiments, the sodium aluminosilicate may be characterized by a pH value of from about 6 to about 12, in other embodiments from about 8 to about 11, and in other embodiments from about 9.5 to about 10.5. As the skilled person appreciates, the pH value can be determined at 5% in water as per ISO 787-9.

Sodium aluminosilicates used in the practice of the present invention are commercially available. For example, they can be purchased under the tradename Sipernat™ (Evonik), including those under the tradenames Sipernat® 320, Sipernat® 320 DS, Sipernat® 360, Sipernat® 500 LS, Sipernat® 2200, Sipernat® 22, Sipernat® 22 S, Sipernat® 22 LS, Sipernat® 50, Sipernat® 50 S, Sipernat® C 600, Sipernat® C 630, Sipernat® 820 A, and Sipernat® 880.

Binder System

Practice of one or more embodiments of the present invention is not limited by the binder system employed. In one or more embodiments, the constituents that form the binder may include conventional constituents used to form liquid coating compositions. Included among useful liquid coating compositions are polymeric compositions including, but not limited to, polyurethane coating compositions, polymeric resin coating compositions.

As suggested above, the binders derive from liquid compositions (e.g. solutions, dispersion, suspensions, or emulsions), which refers to the fact that the compositions are in the liquid state at conditions of temperature and pressure.

In one or more embodiments, the binder is a polymeric resin coating composition. These coating compositions may also be referred to binder compositions or film-forming compositions. In one or more embodiments, these coating compositions include acrylic resins, vinyl acetate resins, halogen addition resins, and/or vinyl acrylic resins. The term acrylic resin is used in its broadest sense and includes polymers and copolymers prepared from polymerizing monomer including acrylic acid, methacrylic acid, acrylates, methacrylates, acrylamides, methacrylimdes, and/or acrylonitrile. In one or more embodiments, the binder compositions are non-reactive compositions. In other embodiments, the resin coating compositions are reactive compositions. In one or more embodiments, the binders derive from compositions that are in the form of a latex.

In one or more embodiments, the polymeric resin composition includes polymer characterized by a number average molecular weight that is greater than 10 kg/mol, in other embodiments greater than 25 kg/mol, and in other embodiments greater than 50 kg/mol. In these or other embodiments, the polymer may be characterized by a number average molecular weight of from about 10 to about 500 kg/mol, in other embodiments from about 25 to about 300 kg/mol, and in other embodiments from about 50 about 200 kg/mol.

Additional Constituents of Indicator Composition

In one or more embodiments, the indicator composition may include additional constituents that may be dispersed throughout the binder matrix or that may additionally form part of the matrix. These constituents may generally include pigments, antioxidants, antiozanants, extenders, and fillers.

Preparation of Indicator Composition

In one or more embodiments, the indicator composition derives from a liquid coating or binder composition that includes a solvent in which the solid constituents (e.g. porous particles and binder) are dissolved, suspended, dispersed or emulsified.

In one more embodiments, the solvent of the liquid coating composition may include water, and these systems may be referred to as water-borne compositions or, in certain embodiments, latexes. In certain embodiments, the water-borne composition may include complementary solvents such as, but not limited to, glycol ethers. Examples of useful glycol ethers include ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, diethylene glycol monomethyl ether, diethylene glycol monoethyl ether, and diethylene glycol mono-n-butyl ether. An exemplary glycol ether is Glycol Ether EB by LyondellBasell.

Preparation of Liquid Binder Composition

In one or more embodiments, the liquid binder compositions may generally be prepared by using conventional techniques for forming these compositions. In general, and as those skilled in the art appreciate, the various constituents of the liquid coating compositions may be introduced and mixed. Where applicable, the mixing may take place at elevated temperatures. For example, the constituents may be mixed at temperatures including room temperature to elevated temperatures as appropriate.

Indicator Structure

As described above, the indicator of the present invention includes a component that contains therein the porous ceramic particles. In one or more embodiments, this component may include a dried or cured layer of the indicator composition described above. This layer may be carried directly by the rubber article, or in other embodiments the layer may be carried by an intermediate substrate that is attached to the rubber article.

An example of an indicator according to the present invention can be described with reference to FIG. 1, which shows tire 10 having disposed directly thereon a dried or cured layer 12 of the indicator composition. Layer 12, as shown in the drawing, is configured or printed to read CHANGE TIRE. Those skilled in the art appreciate that practice of the present invention is not limited by the configuration or print of the indicator composition and therefore a variety of shapes or configurations or texts can be employed. Layer 12, as shown in FIG. 1, is devoid or substantially devoid of fluids that change the optical properties of the composition (i.e., change the optical properties of the ceramic particles within the composition), and therefore layer 12 is visible, especially against the black tire sidewall.

Figure 2:
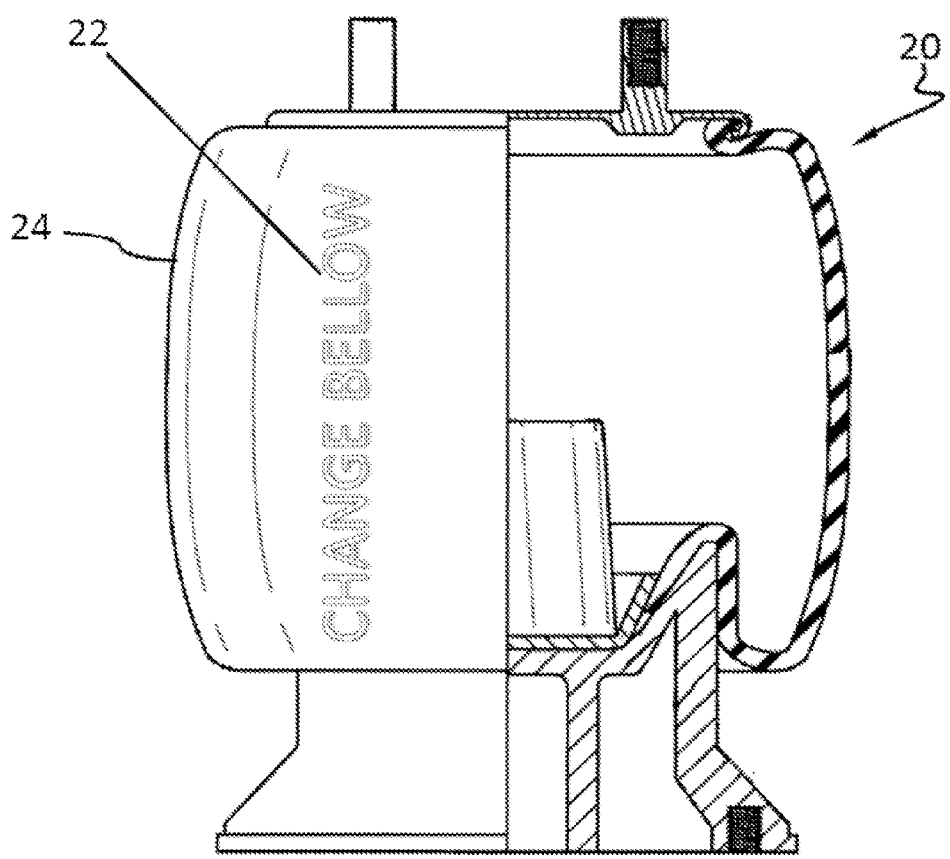
FIG. 2 is a perspective view of an airspring according to one or more embodiments of the present invention.

In another embodiment, which is shown in FIG. 2, an airspring 20 has disposed directly thereon a dried or cured layer 22 of the indicator composition. Specifically, layer 22 is deposited on bellow cover 24.

Figure 3:
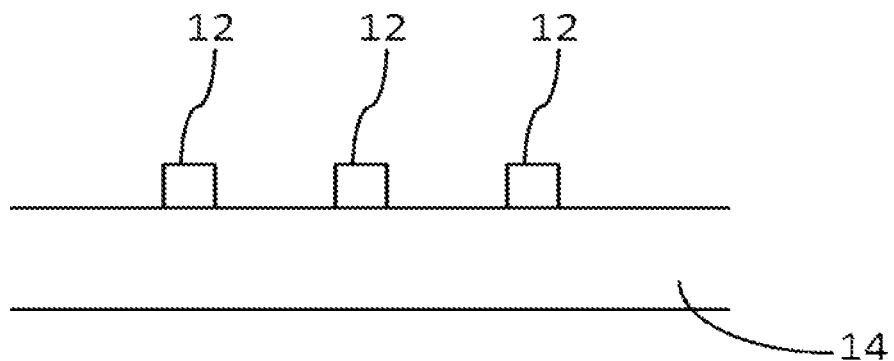
FIG. 3 is a cross-sectional view of a tire or an airspring according to one or more embodiments of the present invention.
Figure 4:
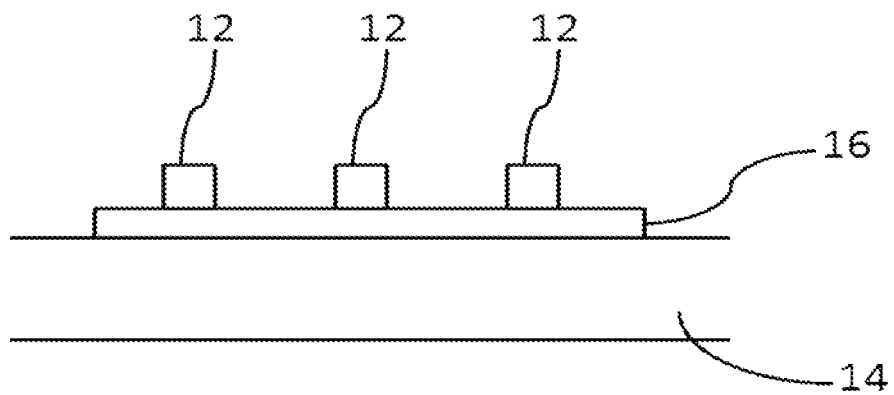
FIG. 4 is a cross-sectional view of a tire or an airspring according to one or more embodiments of the present invention.

As shown in FIG. 3, layer 12 (or 22) is deposited directly on sidewall 14 (or bellow cover 24). In alternative embodiments, as shown in FIG. 4, layer 12 (or 22) is deposited on an intermediate layer 16, which may include an adhesive layer, and layer 16 is adhered to sidewall 14 (or bellow cover 24).

Preparation of Indicator

As described above, at least one component of the indicator is prepared from the indicator composition. In one or more embodiments, these compositions are a liquid or are at least flowable due to the presence of a solvent in which the solids ingredients of the composition are either dissolved or dispersed. The composition is applied to a rubber substrate or an intermediate substrate in a desired design, pattern, or configuration to form a wet or curable coating on the substrate. Upon curing, which may simply include drying or evaporation of the solvent, the wet coating forms a cured or dried coating or layer on the substrate or intermediate substrate. As described above, the cured or dried coating or layer has dispersed therein the porous ceramic particulates in accordance with the invention.

Practice of the invention is not necessarily limited by the techniques employed to apply the liquid or flowable indicator composition to the substrate. Indeed, the skilled person could tailor the composition to a variety of viscosities that will enable the skilled person to use a variety of techniques for applying the composition to a substrate. In one or more embodiments, the composition is applied to the substrate by employing brushing or roller techniques. In other embodiments, printing techniques, may be employed.

In one or more embodiments, the cured coating is then treated with the desired liquid to thereby at least partially saturate the porous ceramic particles. Practice of the present invention is not necessarily limited by the techniques employed to apply the liquid (e.g., oil) to the cured coating. In one or more embodiments, the liquid is applied by brushing or rolling.

In one or more embodiments, after saturating the cured coating with the liquid, a protective film may be applied over the indicator in order to inhibit evaporation of the liquid from the porous ceramic particles. This protective film may include those generally known in the art including thermoplastic films and coated papers. For example, polypropylene or polyethylene films may be used. In other embodiments, paper coated with fluorinated polymers or polysiloxanes may be employed.

Partial Saturation of Particles

The porous particles, at the beginning of the service life of the indicator, are at least partially saturated with a liquid (e.g., an oil) which thereby renders the otherwise opaque or substantially opaque porous particles to be transparent. In other words, the porous ceramic particles adsorb sufficient fluid to change the optical properties of the particles. Without wishing to be bound by any particular theory, it is believed that where the refractive index of the liquid is similar to the refractive index of the porous ceramic particles, the ability of the saturated particles to refract light is reduced, which thereby makes the particles transparent. Also, the refractive index of the porous ceramic particles should differ from the refractive index of the pores as filled with air, which has a refractive index n=1.0003.

Liquid

In one or more embodiments, the fluid employed to at least partially saturate the particles has a refractive index that is within at least 10.0 percent, in other embodiments at least 5.0 percent, and in other embodiments at least 1.0 percent of the refractive index of the porous ceramic particles.

In one or more embodiments, the liquid employed to at least partially saturate the ceramic particles has a refractive index in the range from about 1.36 to about 1.56, in other embodiments from about 1.41 to about 1.51, and in other embodiments from about 1.45 to about 1.47. In one or more embodiments, the index of refraction of the liquid is about 1.46.

In one or more embodiments, the liquid employed to at least partially saturate the ceramic particles is characterized by a viscosity of at least 25, in other embodiments at least 40, and in other embodiments of at least 55 cP at standard conditions of temperature and pressure. In these or other embodiments, the liquid fluid employed to at least partially saturate the ceramic particles has a viscosity in the range from about 25 to about 125, in other embodiments from about 40 to about 105, and in other embodiments from about 55 to about 90 cP at standard conditions of temperature and pressure.

In one or more embodiments, the fluid employed to at least partially saturate the ceramic particles is a hydrocarbon oil. In one or more embodiments, these oils include high-boiling hydrocarbons. Examples of high-boiling hydrocarbon oils included paraffinic oils, aromatic oils, naphthenic oils, vegetable oils, and low PCA oils including MES, TDAE, and SRAE, heavy naphthenic oils, white oils, 2-cycle engine oils, and various synthetic oils such as, but not limited to, polybutene oils.

INDUSTRIAL APPLICABILITY

As described above, the indicators of the present invention may be used in conjunction with rubber articles such as tires and airsprings. In one or more embodiments, the indicator composition can be applied to the tire or the bellow of an airspring after curing the tire or bellow. In particular embodiments, the indicator composition can be applied at the factory where the tire is manufactured. The liquid can be applied to the indicator composition at the same time or down stream in the tire distribution scheme. For example, a liquid can be applied at the point of sale and/or installation of the tire. As suggested above, where the liquid is applied to the indicator composition in advance of sale and/or installation of the tire or bellow, evaporation of the liquid can be inhibited by the use of a protective coating layer that can be removed at the time of installation and/or sale.

EXAMPLES

Example 1

30 parts weight percent of an acrylic adhesive formula, Joncryl 624, by BASF, 5 weight percent of glycol ether EB, 30 weight percent of Sipernat 820 A manufactured by Degussa and 35 weight percent of water are blended together to obtain an opaque white viscous mass. This is used to print a message or an area on a black or colored fabric or another surface of interest and dried. The printed message or area will be white or of other color when dry. Semtol 350 obtained from Sonneborn is spread or sprayed on the message on the printed area; the message or the printed area will turn black or another color of the fabric or substrate and merge with the background of the label or the substrate. The label is provided with an adhesive on the opposite side to attach to the object on which the predetermined time need be displayed. When the predetermined time elapses the label will display the message or the printed area appears in white or another color, that indicates the predetermined time has elapsed.

Example 2

The ink made as in Example 1 is used to print a message, such as "CHANGE TIRE" directly on the substrate such as a tire and allowed to dry the print will be white. This it is covered with a few drops of 2-cycle engine oil; the print will change to black and it will be almost invisible. At the expiration of the predetermined period of time, the message "CHANGE TIRE" will appear in white.

Example 3

The ink described in Example 1 is enhanced with the addition of 5 weight percent of Colorsine concentrate Red after reducing 5 weight of water. The ink so made will be red in color. This ink is sued to print on a label or substrate and dried. Struktol is applied on the opposite side in order to attach it to an object such as tire. At the end of the predetermined period the red color will appear.

Various modifications and alterations that do not depart from the scope and spirit of this invention will become apparent to those skilled in the art. This invention is not to be duly limited to the illustrative embodiments set forth herein.

What is claimed:

1. A rubber article comprising:
   a. a rubber substrate; and
   b. an indicator carried by said rubber substrate, said indicator including at least one component including porous ceramic particles that are at least partially saturated with a liquid, where the particles are transparent when at least partially saturated with the liquid.

2. The indicator of claim 1, where the rubber article is a tire.
3. The indicator of claim 2, where the rubber substrate is a tire sidewall.
4. The indicator of claim 1, where the rubber article is an airspring bellow.
5. The indicator of claim 4, where the rubber substrate is an outer cover of the bellow.
6. The indicator of claim 2, where the porous ceramic particles are porous silica or silicates.
7. The indicator of claim 2, where the porous ceramic particles are sodium aluminosilicates.
8. The indicator of claim 2, where the liquid is a hydrocarbon oil.
9. The indicator of claim 2, where the porous ceramic particles are dispersed within a binder matrix.
10. The indicator of claim 9, where the binder matrix includes a binder resin.
11. The indicator of claim 10, where the binder resin is an acrylic resin.
12. The indicator of claim 4, where the porous ceramic particles are porous silica or silicates.
13. The indicator of claim 4, where the porous ceramic particles are sodium aluminosilicates.
14. The indicator of claim 4, where the liquid is a hydrocarbon oil.
15. The indicator of claim 4, where the porous ceramic particles are dispersed within a binder matrix.
16. The indicator of claim 15, where the binder matrix includes a binder resin.
17. The indicator of claim 16, where the binder resin is an acrylic resin.

* * * * *